United States Patent [19]

Brownell et al.

[11] Patent Number: 4,916,248

[45] Date of Patent: Apr. 10, 1990

[54] SILYL DERIVATIVES OF 2, 6-DIMETHYL-4-ALLYL PHENOL

[75] Inventors: George L. Brownell, Pittsburgh; Mary K. Hays, Turtle Creek; Andrew J. Sivak, Edgewood Boro, all of Pa.

[73] Assignee: Aristech Chemical Corporation, Pittsburgh, Pa.

[21] Appl. No.: 375,644

[22] Filed: Jul. 5, 1989

[51] Int. Cl.$^4$ ................................. C07F 7/08
[52] U.S. Cl. ..................................... 556/486
[58] Field of Search ........................... 556/486

[56] References Cited

U.S. PATENT DOCUMENTS 2,611,778  9/1952  Speier .................................. 556/486
3,489,783  1/1970  Shepard et al. ................. 556/486 X
4,783,495  11/1988  Pastor et al. ..................... 556/486 X

FOREIGN PATENT DOCUMENTS 0001190  1/1985  Japan ................................. 556/486
0023384  2/1985  Japan ................................. 556/486

Primary Examiner—Paul F. Shaver
Attorney, Agent, or Firm—William L. Krayer

[57] ABSTRACT

Silyl derivatives of 2,6 dimethyl, 4-allyl phenol include compositions of the formula

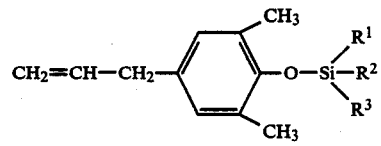

where $R^1$, $R^2$ and $R^3$ are independently selected from alkyl and phenyl groups having up to about eight carbon atoms. They may be made by silylating the corresponding hydroxyl compound. They are useful as co-monomers for olefins to introduce functional sites in high molecular weight copolymers.

4 Claims, No Drawings

SILYL DERIVATIVES OF 2,6-DIMETHYL-4-ALLYL PHENOL

TECHNICAL FIELD

This invention relates to new silyl derivatives of a certain substituted phenol, specifically to silyl derivatives of 2,6-dimethyl-4-allyl phenol. In particular, it relates to compositions of the formula

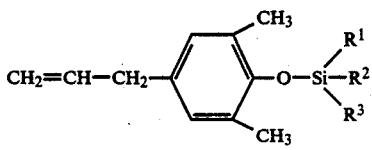

wherein $R^1$, $R^2$ and $R^3$ are independently selected from linear, branched and cyclic hydrocarbon groups having from one to about eight carbon atoms.

BACKGROUND ART

In U.S. patent application Ser. No. 047,960 (see corresponding PCT International Publication No. WO88/08856, Nov. 17, 1988), it is disclosed that comonomers for propylene may be made by protecting the oxygen of a copolymerizable hydroxy-containing compound by substituting the hydrogen thereof with a silyl group having at least some steric bulk, i.e., at least about three carbon atoms in separate groups surrounding it.

Silylated monomers of the general formula

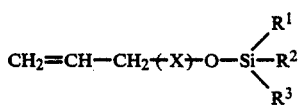

are suggested in the above-referenced publication.

The peculiar advantage, however, of 2,6 dimethyl 4-allyl phenol as a potential comonomer in its silylated form apparently has not been seen in the prior art.

The compound 2,6 dimethyl, 4-allyl phenol is known. See Tarbell, D. Stanley, and Kincaid, John F. JACS, 62, 1940, 728-31.

DISCLOSURE OF INVENTION

The invention herein is a series of new compounds of the formula

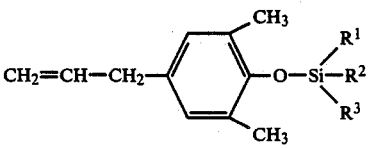

where $R^1$, $R^2$ and $R^3$ are independently selected from linear, branched and cyclic hydrocarbon groups having from one to about eight carbon atoms. They are useful as comonomers for propylene to insert units having reactive sites into the polymer chain where highly active Ziegler-Natta catalyst may otherwise prevent such insertion.

Following are examples of the preparation of such compounds.

All operations were performed under inert atmosphere using standard Schlenk techniques. All liquid reagents and solvents were purged with inert gas prior to their introduction into the reaction system.

EXAMPLE 1

(2,6-dimethyl-4-allyl) phenoxy diphenylmethyl silane 32.700 g (0.202 mol) of 2,6-dimethyl-4-allyl phenol were added to a 250 ml flask with an Argon inlet followed by 0.325 g (0.014 mol) sodium. After one-half hour of stirring, the sodium had completely reacted and 45.569 g (0.188 mol) of diphenylmethyl (ethoxy) silane were added to this mixture. Stirring continued for one hour at which time a reflux condenser was attached and the solution was heated for 4 hours. vacuum distillation at 1 mm Hg and gas chromatographic mass spectral analysis of the resultant collections indicated that none of the desired product had formed. The first two fractions contained the phenol and these were recombined in a 250 ml Schlenk flask and 0.2 g sodium were added followed by 50 ml of tetrahydrofuran (which promoted reaction of the sodium). The solution was homogeneous after 1 hour of stirring and the third fraction (from vacuum distillation), which had been found to contain the silane, was added to the solution. A reflux condenser was attached and the mixture was heated for about 6 hours (variac settings were from 40-70). Some dark precipitate was observed at that time and the heating was discontinued for fear of decomposition. Vacuum distillation of this mixture produced three fractions of which the highest boiling (112°-190° C. at 1 mm Hg was found to contain the desired product. The product's identity was confirmed by $^1$H NMR and gas chromatography and the yield was 3.5 g (5%).

EXAMPLE 2

(2,6-dimethyl-4-allyl)phenoxy dimethylethyl silane 12.888 g (0.068 mol) of 2,6-dimethyl-4-allyl phenol were added to a 500 ml flask with an Argon inlet and a cool water bath was applied. 1.56 g (0.068 mol) of sodium were cut into small pieces and were added to this cooled solution. This mixture was allowed to slowly warm to room temperature while stirring for four hours. At this time, 30 ml of tetrahydrofuran were added in order to encourage complete reaction of the sodium, and stirring was continued overnight.

8.500 g (0.069 mol) of dimethylethyl (chloro) silane were then added dropwise through an additional funnel. The resultant mixture was stirred for 5 hours at which time 250 ml of heptane were added and the precipitate was allowed to settle over the next day. The NaCl was removed by filtration of the colloid through filter paper and then through fritted glass/Celite. The product distilled at 120°-122° C. (1 mm Hg) with a yield of 5 g (30%).

A general procedure for copolymerizing our new compounds with ethylene or propylene follows:

Standard inert atmosphere techniques were used to exclude moisture and oxygen throughout the manipulations recited below.

A round bottom flask fitted with a side arm, magnetic stirring bar and a stopper, which apparatus had been assembled hot from a drying oven and was then either evacuated and refilled with inert gas several times or (and) purged with the inert gas for at least 15 minutes, was charged with a given amount of solvent, heptane or toluene, usually 125 ml. The solvents were freshly distilled from sodium and triethyl aluminum (TEA) over which they had been refluxing for at least 18 hours under an inert atmosphere. Immediately after the solvent had been charged to the flask, alkyl aluminum co-catalyst, which was in the form of a heptane solution of about 25 wt % (0.715 g/ml in heptane), was also added to the flask which was then lowered into a thermostated oil bath and magnetic stirring was begun.

At this point the inert gas atmosphere in the flask was replaced with the gaseous comonomer by a minimum of 3 cycles of evacuation and refilling back to atmospheric pressure with the comonomer. After the third cycle, the solution was stirred for at least 10 minutes (usually longer) to allow the solvent to become saturated with the comonomer. Pressure was maintained at about one atmosphere via a bubbler.

Next were added an "external donor", which usually was diphenyl dimethoxy silane or phenyl triethoxy silane, if one was being used, and the other comonomer. The polymerization was initiated by the addition of the transition metal containing co-catalyst, which was a titanium tetrachloride on a magnesium chloride support.

As the gaseous comonomer was consumed it was replaced by maintaining the pressure constant at one atmosphere via a bubbler.

After a specified period of time (generally about two hours) the reaction was quenched by the addition of acidified alcohol (HCl in iso-propanol, ethanol, and/or methanol). The quenched reaction slurry was combined with the alcohol solution of volume at least twice the original volume of the inert reaction solvent. The resultant slurry was stirred for at least 45 minutes and then filtered. This treatment not only stopped the reaction, it dissolved catalyst residues and removed the silyl groups and thus regenerated the hydroxyl groups.

If the filtration proceeded very slowly, the slurry was combined with enough water to make the filtration proceed at a convenient rate.

The polymer was resuspended in alcohol, stirred, filtered and vacuum dried overnight. Boiling heptan soluble content was determined by standard methods.

The utility of our new compounds as comonomers for lower olefins is thus demonstrated. Functional substitutes such as dyes may be placed on the regenerated hydroxyl groups in the copolymer chain.

EXAMPLE 3

For the copolymerization of propylene and (2,6-dimethyl-4-allyl) phenoxy diphenylmethyl silane, the following specific procedure was used:

A 500 ml flask with a sidearm was evacuated and refilled with argon three times. To this flask were added 75 ml of dry, degassed heptane and the solvent was saturated with propylene. 3.23 ml of triethylaluminum co-catalyst (0.715 g/ml in heptane) were then added to this solution followed by 3.60 ml (0.010 mol) of (2,6-dimethyl-4-allyl) phenoxy diphenylmethyl silane and the flask was placed in an oil bath which had been maintained at 50° C.

The polymerization was initiated by the addition of 0.075 g of titanium co-catalyst and the mixture was stirred for two hours at which time it was quenched by the addition of approximately 300 ml of acidified isopropanol. The alcoholic solution was allowed to stir for 1.5 hours prior to filtration of the polymer. Resuspension of the product in isopropanol and stirring for 15 minutes provided the final wash for the polymer. The product was then filtered and vacuum dried.

We claim:

1. A compound of the formula

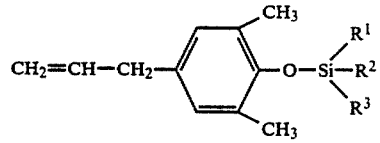

in which $R^1$, $R^2$ and $R^3$ are independently selected from linear, branched and cyclic hydrocarbon groups having from one to about eight carbon atoms.

2. (2,6-dimethyl-4-allyl) phenoxy tri-iso-propyl silane.

3. (2,6-dimethyl-4-allyl) phenoxy methyldiphenyl silane.

4. (2,6-dimethyl-4-allyl) phenoxy dimethylethyl silane.

* * * * *